(12) United States Patent  
Chang et al.

(10) Patent No.: US 8,206,740 B2  
(45) Date of Patent: *Jun. 26, 2012

(54) ONCE DAILY FORMULATIONS OF TETRACYCLINES

(75) Inventors: Rong-Kun Chang, Rockville, MD (US); Arash Raoufinia, Springfield, VA (US); Niraj Shah, Owings Mills, MD (US)

(73) Assignee: Supernus Pharmaceuticals, Inc., Rockville, MD (US)

( * ) Notice: Subject to any disclaimer, the term of this patent is extended or adjusted under 35 U.S.C. 154(b) by 626 days.

This patent is subject to a terminal disclaimer.

(21) Appl. No.: 12/155,676

(22) Filed: Jun. 6, 2008

(65) Prior Publication Data

US 2009/0011006 A1  Jan. 8, 2009

Related U.S. Application Data

(63) Continuation of application No. 10/819,620, filed on Apr. 7, 2004, now Pat. No. 7,749,532.

(60) Provisional application No. 60/460,963, filed on Apr. 7, 2003, provisional application No. 60/547,964, filed on Feb. 26, 2004.

(51) Int. Cl.  
*A61K 9/54* (2006.01)

(52) U.S. Cl. ........................................... 424/458

(58) Field of Classification Search ................ None  
See application file for complete search history.

(56) References Cited

U.S. PATENT DOCUMENTS

| | | |
|---|---|---|
| 4,293,539 A | 10/1981 | Ludwig et al. |
| 4,666,897 A | 5/1987 | Golub et al. |
| 4,704,383 A | 11/1987 | McNamara et al. |
| 4,837,030 A | 6/1989 | Valorose, Jr. et al. |
| 4,935,411 A | 6/1990 | McNamara et al. |
| 4,935,412 A | 6/1990 | McNamara et al. |
| 5,045,538 A | 9/1991 | Schneider et al. |
| 5,122,519 A | 6/1992 | Ritter |
| 5,167,964 A | 12/1992 | Muhammad et al. |
| 5,188,836 A | 2/1993 | Muhammad et al. |
| 5,223,248 A | 6/1993 | McNamara et al. |
| 5,238,686 A | 8/1993 | Eichel et al. |
| 5,258,371 A | 11/1993 | Golub et al. |
| 5,260,292 A | 11/1993 | Robinson et al. |
| 5,277,916 A | 1/1994 | Dwyer et al. |
| 5,283,065 A | 2/1994 | Doyon et al. |
| 5,286,497 A | 2/1994 | Hendrickson et al. |

(Continued)

FOREIGN PATENT DOCUMENTS

EP        0 410 099 A1    1/1991

(Continued)

OTHER PUBLICATIONS

Notice of Allowance mailed on Apr. 29, 2010, in prior U.S. Appl. No. 10/819,620, 7 pages.

(Continued)

*Primary Examiner* — Paul Dickinson  
(74) *Attorney, Agent, or Firm* — Foley & Lardner LLP; Stephen B. Maebius; Sunit Talapatra

(57) ABSTRACT

Disclosed are once-daily formulations containing tetracyclines, especially doxycycline. Such formulations are useful, for instance, for the treatment of collagenase destructive enzyme-dependent diseases, such as periodontal disease and acne, and acute and chronic inflammatory disease states, such as rosacea and arthritis.

29 Claims, 6 Drawing Sheets

Dissolution profile for doxycycline monohydrate IR beads

U.S. PATENT DOCUMENTS

| | | | |
|---|---|---|---|
| 5,300,304 | A | 4/1994 | Sheth et al. |
| 5,308,839 | A | 5/1994 | Golub et al. |
| 5,321,017 | A | 6/1994 | Golub et al. |
| RE34,656 | E | 7/1994 | Golub et al. |
| 5,348,748 | A | 9/1994 | Sheth et al. |
| 5,413,777 | A | 5/1995 | Sheth et al. |
| 5,449,688 | A | 9/1995 | Wahl et al. |
| 5,459,135 | A | 10/1995 | Golub et al. |
| 5,505,949 | A | 4/1996 | Benitez |
| 5,517,049 | A | 5/1996 | Huang |
| 5,523,297 | A | 6/1996 | Pruzanski et al. |
| 5,532,227 | A | 7/1996 | Golub et al. |
| 5,674,539 | A | 10/1997 | Tomas |
| 5,753,711 | A | 5/1998 | Schwabe et al. |
| 5,770,588 | A | 6/1998 | McNamara et al. |
| 5,773,430 | A | 6/1998 | Simon et al. |
| 5,789,395 | A | 8/1998 | Amin et al. |
| 5,792,446 | A | 8/1998 | Ashley |
| 5,827,503 | A | 10/1998 | Schwabe |
| 5,827,840 | A | 10/1998 | Ramamurthy et al. |
| 5,834,449 | A | 11/1998 | Thompson et al. |
| 5,837,696 | A | 11/1998 | Golub et al. |
| 5,908,838 | A | 6/1999 | Gans |
| 5,919,775 | A | 7/1999 | Amin et al. |
| 5,929,055 | A | 7/1999 | Ryan et al. |
| 5,977,091 | A | 11/1999 | Nieman et al. |
| 5,998,390 | A | 12/1999 | Ramamurthy et al. |
| 6,015,803 | A | 1/2000 | Wirostko |
| 6,015,804 | A | 1/2000 | Golub et al. |
| 6,043,231 | A | 3/2000 | Pruzanski et al. |
| 6,100,248 | A | 8/2000 | Golub et al. |
| 6,114,316 | A | 9/2000 | Ramamurthy et al. |
| 6,133,310 | A | 10/2000 | Parks |
| 6,143,506 | A | 11/2000 | Golub et al. |
| 6,217,904 | B1 | 4/2001 | Midha et al. |
| 6,228,398 | B1 | 5/2001 | Devane et al. |
| 6,322,819 | B1 | 11/2001 | Burnside et al. |
| 6,344,215 | B1 | 2/2002 | Bettman et al. |
| 6,372,255 | B1 | 4/2002 | Saslawski et al. |
| 6,455,583 | B1 | 9/2002 | Pflugfelder et al. |
| 6,485,746 | B1 | 11/2002 | Campbell et al. |
| 6,500,457 | B1 | 12/2002 | Midha et al. |
| 6,506,740 | B1 | 1/2003 | Ashley et al. |
| 6,610,274 | B1 | 8/2003 | Gardner |
| 6,638,922 | B2 | 10/2003 | Ashley et al. |
| 6,663,888 | B2 | 12/2003 | Percel et al. |
| 6,664,287 | B2 | 12/2003 | Avery et al. |
| 6,673,843 | B2 | 1/2004 | Arbiser |
| 6,730,320 | B2 | 5/2004 | Rudnic et al. |
| 6,913,768 | B2 | 7/2005 | Couch et al. |
| 6,953,593 | B2 | 10/2005 | Kuhrts et al. |
| 7,008,631 | B2 | 3/2006 | Ashley |
| 7,014,858 | B2 | 3/2006 | Ashley |
| 7,211,267 | B2 | 5/2007 | Ashley |
| 7,232,572 | B2 | 6/2007 | Ashley |
| 2002/0004499 | A1 | 1/2002 | Rudnic et al. |
| 2002/0136766 | A1* | 9/2002 | Rudnic et al. ............ 424/457 |
| 2003/0082120 | A1 | 5/2003 | Milstein |
| 2003/0096008 | A1 | 5/2003 | Rudnic et al. |
| 2003/0130240 | A1 | 7/2003 | Ashley |
| 2003/0139380 | A1* | 7/2003 | Ashley ..................... 514/152 |
| 2004/0014731 | A1 | 1/2004 | Golub et al. |
| 2004/0063674 | A1 | 4/2004 | Levy et al. |
| 2004/0115261 | A1 | 6/2004 | Ashley |
| 2004/0142035 | A1 | 7/2004 | Chang et al. |
| 2004/0147492 | A1 | 7/2004 | Ashley |
| 2006/0094697 | A1 | 5/2006 | Ashley |

FOREIGN PATENT DOCUMENTS

| | | |
|---|---|---|
| EP | 0 464 932 B2 | 1/1992 |
| JP | 02-006437 A | 1/1990 |
| WO | WO 83/00628 A1 | 3/1983 |
| WO | WO 96/16648 A1 | 6/1996 |
| WO | WO 98/05340 A1 | 2/1998 |
| WO | WO 99/58131 A1 | 11/1999 |
| WO | WO 00/18353 A2 | 4/2000 |
| WO | WO 00/23055 A1 | 4/2000 |
| WO | WO 01/87823 A1 | 11/2001 |
| WO | WO 02/080932 A1 | 10/2002 |
| WO | WO 02/083106 A1 | 10/2002 |

OTHER PUBLICATIONS

Oracea (doxycycline, USP) Capsules 40 mg brochure, Galderma Laboratories, L.P., May 2008, 2 pages.

Gunsel and Dusel, Chapter 5, "Compression-coated and layer tablets," Pharmaceutical Dosage Forms: Tablets, Second Edition, vol. 1, Edited by H.A. Lieberman et al., 1990.

Remington's Pharmaceutical Sciences, 18$^{th}$ Edition, Gennaro, Ed., 1990, Chapters 88-91.

Elewski et al., Journal of the American Academy of Dermatology, 1983, vol. 8, pp. 807-812.

Plewig et al., Journal of Investigative Dermatology, 1975, vol. 65, p. 532.

Ryan et al., "Potential of Tetracycline to Modify Cartilage Breakdown in Osteoarthritis," Current Opinion in Rheumatology, 1996, vol. 8, pp. 238-247.

Wong et al., Journal of American Academy of Dermatology, 1984, vol. 1, pp. 1076-1081.

Berger, Richard S., M.D., "A Double-Blind, Multiple-Dose, Placebo-Controlled, Cross-Over Study to Compare the Incidence of Gastrointestinal Complaints in Healthy Subjects Given Doryx R and Vibramycin R," J. Clin. Pharmacol., 1988, 28:367-370.

Doryx entry, Physicians' Desk Reference, 2002, 3357-3358.

Garnett et al., "Pharmacokinetic Evaluation of Twice-Daily Extended-Release Carbamazepine (CBZ) and Four-Times-Daily Immediate-Release CBZ in Patients with Epilepsy," Epilepsia, 1998, 39(3):274-279.

McLean et al., "The Influence of Food on the Bioavailability of a Twice-Daily Controlled Release Carbamazepine Formulation," J. Clin. Pharmacol., 2001, 41:183-186.

Press Release, Aug. 13, 2002, "CollaGenex launches Phase 3 study of Periostat as Rosacea treatment," 1 page.

Press Release, Apr. 1, 2003, Low-dose doxycycline emerges for acne, rosacea (Off-Label Studies), 2 pages.

Press Release, Jul. 25, 2003, "CollaGenex Pharmaceuticals Reports Progress with Development of Sustained Release Once-Daily Periostat Formulation; Formulation Selected and Initial Phase 1 Studies Complete," 3 pages.

Pandey et al., "In vitro study on capsule formulations of omeprazole containing enteric coated granules," Boll. Chim. Farmac., Nov./Dec. 2002, 141(6):419-422.

Periostat (doxycycline hyclate tablets) 20mg prescribing information, Feb. 1, 2001, 16 pages.

Solodyn FDA approval package, May 8, 2006, 32 pages.

Tulloch et al., "SLI381 (Adderall XR), a Two-Component, Extended-Release Formulation of Mixed Amphetamine Salts: Bioavailability of Three Test Formulations and Comparison of Fasted, Fed, and Sprinkled Administration," Pharmacotherapy, 2002, 22(11):1405-1415.

Vibramycin entry, Physicians' Desk Reference, 2002, 2735-2736.

Office Action mailed on Aug. 4, 2009, in prior U.S. Appl. No. 10/819,620, 12 pages.

http://www.drugs.com/doxycycline.html, accessed Jul. 25, 2009, 7 pages.

U.S. Appl. No. 12/926,932, filed Dec. 17, 2010, Chang et al.
U.S. Appl. No. 12/926,933, filed Dec. 17, 2010, Chang et al.
U.S. Appl. No. 12/926,934, filed Dec. 17, 2010, Chang et al.

"Humans Have Ten Times More Bacteria Than Human Cells: How Do Microbial Communities Affect Human Health," ScienceDaily (Jun. 5, 2008), http://www.sciencedaily.com/releases/2008/06/080603085914.htm, 3 pages.

Adams et al., "Topical Fusidic Acid Versus Peroral Doxycycline in the Treatment of Patients with Acne Vulgaris of the Face," Cur. Therapeutic Res. (1991) 50(2):268-273.

Akamatsu et al., "Effect of Doxycycline on the Generation of Reactive Oxygen Species: A Possible Mechanism of Action of Acne Therapy with Doxycycline," Acta. Derm. Venereol. (Stockh) (1992) 72:178-179.

Akamatsu et al., "Effect of Keigai-Rengyo-To, a Japanese Kampo Medicine, on Neutorphil Functions: a Possible Mechanism of Action of Keigai-Rengyo-To in Acne," *J. Int'l Med. Res.* (1997) 25:255-265.

Akamatsu et al., "Effect of subminimal inhibitory concentrations of minocycline on neutrophil chemotactic factor production in comedonal bacteria, neutrophil phagocytosis and oxygen metabolism," Arch. Dermatol. Res. (1991) 283:524-528.

Akamatsu et al., "Effects of Subminimal Inhibitory Concentrations of Erythromycin, Tetracycline, Clindamycin, and Minocycline on the Neutrophil Chemotactic Factor Production in Propionibacterium acnes Biotypes 1-5", The Journal of Dermatology, (1991), 18, 247-251.

Akpek et al., "Ocular Rosacea," *Ophthalmology* (Nov. 1997) 104(11):1863-1867.

Amin et al., "A Novel Mechanism of Action of Tetracyclines: Effects on Nitric Oxide Synthases," *Proc. Nat'l Acad. Sci.* (Nov. 1996) 93:14014-14019.

Amin et al., "The Expression and Regulation of Nitric Oxide Synthase in Human Osteoarthritis-affected chondrocytes: Evidence for Up-regulated Neuronal Nitric Oxide Synthase," *J. Exp. Med.* (Dec. 1995) 182:2097-2102.

Baer et al., "High-Dose Tetracycline Therapy in Severe Acne," *Arch. Dermatol.* (Apr. 1976) 112:479-481.

Bartholomew et al., "Oxytetracycline in the Treatment of Ocular Rosacea: A Double-Blind Trial," *Brit. J. Opth.* (1982) 66:386-388.

Batista et al., "Nitric oxide synthesis and severity of human periodontal disease", Oral Diseases (2002) 8, 254-260.

Bikowski et al., "Treatment of rosacea with doxycycline monohydrate," *Cutis* (Aug. 2000) 66:149-152.

Bikowski, J., Examining Inflammation as a Common Factor in Theories of Rosacea Pathophysiology, www.rosacea.com, 2006, (available at http://web.archive.org/web/20080607070740/http://www.rosaceatoday.com/TheoriesofRosacea.asp).

Bodokh et al., "Minocycline Induces an Increase in the Number of Excreting Pilosebaceous Follicles in Acne Vulgaris," *Acta. Derm. Venereol. (Stockh)* (1997) 77:255-259.

Bouwsma et al., "Low Dose Doxycycline: Effects on Clinical Parameters in Adult Periodontitis," *J. Dent. Res.* 71 (AADR Abstracts) (1992) 245, Abstract 1119.

Braun-Falco et al., "Diseases of the Sebaceous Follicles," (1991) *Dermatology* (1d ed.), Ch. 28, Table of Contents and pp. 716-743.

British Nat'l Formulary No. 31 (Mar. 1996) at 241 and 471.

Browning et al., "Ocular rosacea," *Surv. Opthal.* 31:145-158 (1986).

Bruch-Gerharz, D., et al., Nitric oxide and its implications in skin homeostatis and disease—a review, Arch. Dermatol. Res. 290:643-651 (1998).

Caton, J. G., "Evaluation of Periostat for Patient Management," *Compendium* (May 1999) 20(5):451-462.

Chandrasoma, P. and C. Taylor, Concise Pathology, Table of Contents and pp. 34-44 ($1^{st}$ ed. Appelton & Lange 1991).

Clancy et al., "Nitric Oxide: A Novel Mediator of Inflammation," *Proc. Sci. Exp. Biol. Med.* (1995) 210:93-101.

Cotran et al., Robbins Pathologic Basic of Diseases, 40-41 ($4^{th}$ ed. W.B. Saunders Co. 1989).

Cotterill et al., "A Comparison of Trimethoprim-Sulphamethoxazole With Oxytetracycline in Acne Vulgaris," *Br. J. Derm.* (1971) 84:366-369.

Cunha et al., "Pharmacodynamics of Doxycycline," *Clin. Microbiol & Infect.* (May 2000) 6(5):270-273.

Cunliffe et al., "A Comparison of the Efficacy and Safety of Lymecycline and Minocycline in Patients With Moderately Severe Acne Vulgaris," Eur. J. Derm. (1998) 8:161-66.

Cunliffe et al., "Evolution of Strategy for the Treatment of Acne," *J. Am. Acad. Dermatol.* (Mar. 1987) 16(3,1):591-599.

Cunliffe et al., "Tetracycline and Acne Vulgaris: A Clinical and Laboratory Investigation," Br. Med. J. (1973) 4:322-35.

Curtis et al., Biology 725-726 (Worth Publishers, Inc. 1985), Table of Contents.

Davies et al., "Understanding Biofilm Resistance to Antibacterial Agents," *Nat Rev Drug Discov* (Feb. 2003) 2(2):114-122.

Del Rosso "Recently Approved Systemic Therapies for Acne Vulgaris and Rosacea," (Aug. 2007) *Cutis* 80:113-120.

Del Rosso et al., "Classification, Pathophysiology, and Treatment of Rosacea," Cutis 74(3S): 32-34 (Sep. 2004).

Deliconstantinos G., et al., "Release by ultraviolet B (u.v.B) radiation of nitric oxide (NO) from human keratinocytes: a potential role for nitric oxide in erythema production," Br. J. Pharmacol. 114:1257-1265 (1995).

Dorbecker et al., "In vitro susceptibility of Baronella species to 17 animicrobial compounds: comparison of Etest and agar dilution," *J Antimicrob Chemother* (2006) 58:784-788.

Eady et al., "Modulation of Comedonal Levels of Interleukin-1 in Acne Patients Treated with Tetracyclines," *J. Invest. Dermatol.* (Jul. 1993) 101(1):86-91.

Esterly et al., "The Effect of Antimicrobial Agents on Leukocyte Chemotaxis," *J. Invest. Dermatol.* (1978) 70(1):51-55.

Farrell et al., "Increased Concentrations of Nitrite in Synovial Fluid and Serum Samples Suggest Increased NO Synthesis in Rheumatic Diseases," *Ann. Rheum. Dis.* (1992) 51:1219-1222.

Gearing et al., "Processing of Tumour Necrosis Factor—Processing by a Metalloproteinase Inhibitor," *Nature* (Aug. 18, 1994) 370:555-557.

Geller et al., "Cytokines, Endotoxin, and Glucocorticoids Regulate the Expression of Inducible Nitric Oxide Synthase in Jepatocytes," *Proc. Nat'l Acad. Sci.* (Jan. 1993) 90:522-526.

Goldsmith, P.C., et al., "Inhibitors of nitric oxide synthase in human skin," J. Invest. Dermatol. 106(1):113-118 (Jan. 1996).

Golub et al., "A Matrix Metalloproteinase Inhibitor Reduces Bone-Type Collagen Degradation Fragments and Specific Collagenases in Gingival Crevicular Fluid During Adult Periodontitis," *Inflamm. Res.* 46:310-319 (1997).

Golub et al., "A Non-Antibacterial Chemically-Modified Tetracycline Inhibits Mammalian Collagenase Activity," *J. Dent. Res.* (Aug. 1987) 66:1310-1314.

Golub et al., "Host Modulation With Tetracyclines and Their Chemically Modified Analogues," *Curr. Opin. Dent.* (1992) 2:80-90.

Golub et al., "Low-Dose Doxycycline Therapy: Effect on Gingival and Crevicular Fluid Collagenase Activity in Humans," *J. Periodontol. Res.* (1990) 25:321-330.

Golub et al., "Minocycline reduces gingival collagenolytic activity during diabetes," *J. Periodont. Res.* (1983) 18:516-526.

Golub et al., "Tetracyclines Inhibit Connective Tissue Breakdown: New Therapeutic Implications for an Old Family of Drugs," *Crit. Rev. Oral Biol. Med.* (1991) 2(2):297-322.

Golub, L.M. et al., "Low-Dose Minocycline Therapy: Effects on Crevicular Fluid (CF) Collagenase and Subgingival Microflora," 66 (Special Issue) Journal of Dental Research 154 (Abstract 384), 1987.

Golub, L.M., et al., Tetracyclines inhibit connective tissue breakdown by multiple nonantimicrobial mechanisms, Adv. Dent. Res. 12:12-26 (Nov. 1998).

Goodson, "Antimicrobial strategies for treatment of periodontal diseases" *Periodontol 2000* (1994) 5(1):142-168.

Greenstein, et al., "Efficacy of subantimicrobial dosing with doxycycline: Point/Counterpoint," *J. Am. Dental Assoc.* (Apr. 2001) 132:457-466.

Greenwald et al., "Low Dose Doxycycline Inhibits Pyridinoline Excretion in Selected Patients with Rheumatoid Arthritis," *Ann. of NY Acad. Sci.* (1994) 732:419-421.

Greenwald et al., "Tetracyclines inhibit human synovial collagenase in Vivo and in Vitro," *J. Rheumatol.* (1987) 14(1):28-32.

Greenwald et al., "Tetracyclines May Be Therapeutically Beneficial in rheumatoid Arthritis, but Not for the Reasons that You Might Think," *J. Clin. Rheum.* (1995) 1(3):185-189.

Grice et al., "Topographical and Temporal Diversity of the Human Skin Microbiome," *Science* (May 29, 2009) 324:1190-1192.

Gurer, M.A., et al., The seroprevalence of *Helicobacter pylori* and nitric oxide in acne rosacea, Int. J. Dermatol. 41:768-770 (2002).

Guttman, Cheryl, "Emerging resistance changes face to antibiotic therapy for acne," *Dermatol. Times* (Jan. 2001) 22.

Haffajee, et al., "Clinical changes following four different periodontal therapies for the treatment of chronic periodontitis: 1-year results," *J Clin Periodontol* (2007) 34:245-253.

Haffajee, et al., "Microbiological Changes Associated with Four Different Periodontal Therapies for the Treatment of Chronic Periodontitis," Oral Microbiol Immunol (2008) 23:148-157.

Harrison, "A Comparison of Doxycycline and Minocycline in the Treatment of Acne Vulgaris," *Clin. Exp. Derm.* (1988) 13:242-244.

Hoyt et al., "Doxycycline Modulates Nitric Oxide Production in Murine Lung Epithelial Cells," *J. Immun.* (2006) 176:567-572.

Humbert et al., "The Tetracyclines in Dermatology," *J. Am. Acad. Derm.* (Oct. 1991) 25(4):691-697.

Hussar, Daniel A., Ph.D., "Importance of Patient Compliance in Effective Antimicrobial Therapy," *Pediatr. Infect. Dis.* (1987) 6(10):971-975.

Illig, "Positive side effects of antibiotic and antimicrobial therapy for acne," *Infection* 7 (1979) Suppl. 6:584-588, English summary on first page.

Jimenez-Acosta et al., "Response to tetracycline of telangiectasias in male hemophiliac with human immunodeficiency virus infection," *J. Am. Acad. Dermatol.* (1988) 19(2)(Pt. 1):369-370.

Jones, David, M.D., Ph.D., "Reactive oxygen species and rosacea," Cutis 74(3S):17-20 (Sep. 2004).

Jones, Ronald N., M.D., "In Vitro Reference Susceptibility Testing of Key Pathogens Against Doxycycline by CLSI Reference Methods (United States Isolated for 2009)," North Liberty, Iowa: JMI Laboratories; Mar. 22, 2010, 7 pages.

Kharitonov et al., "Increased Nitric Oxide in Exhaled Air of Asthmatic Patients," *Lancet* (Jan. 15, 1994) 343:133-135.

Knight et al., "A follow-up of tetracycline-treated rosacea," *Br. J. Dermatol.* (1975) 93:577-580.

Knox et al., "Demethylchlortetracycline in the Treatment of Acne Vulgaris," *Southern Med. J.* (1965) 58:1056, 1060.

Komman et al., "The Effect of Long-Term Low-Dose Tetracycline Therapy on the Subgingival Microflora in Refractory Adult Periodontitis," *J. Periodontol.* (1982) 53(10):604-610.

Korting et al., "Tetracycline actions relevant to rosacea treatment," Skin Pharmacol. Physiol. 22:287-294 (Sep. 25, 2009).

Lappin et al., Inducible nitric oxide synthase expression in periodontitis, *J. Periodont. Res.* (2000) 35, 369-373.

Laux, "A Comparison of Doxycycline Versus Minocycline," *Hautarzt* (1989) 40:577-81, English summary on first page and full English translation provided.

Lee et al., "Effect of Protein Binding of Daptomycin on MIC and Antibacterial Activity," *Antimicrob Agents Chemother* (Dec. 1991) 35(12):2505-2508.

Levell et al., (not Hayes, N.A., et al.), Nitric oxide synthase in dithranol induced erythema, J. Invest. Dermatol. 103(3):435 (1994), Abstract 232.

Li et al., "Off-Label Dermatologic Therapies: Usage, Risks and Mechanisms," *Arch. Dermatol.* (Nov. 1998) 134:1449-1454.

Lipsky et al., "Treatment of Bacterial Prostatitis," *Clin Infect Dis* (Jun. 15, 2010) 50(12):1641-1652.

Lorian, Victor, M.D., "Some Effects of Sub-inhibitory Concentration of Antibiotics on bacteria," *Bull NY Acad Med* (Oct. 1975) 51(9):1046-1055.

Macsai, M.S. et al., *Chapter 41: Acne Rosacea*, 1(2) Dermatology Online Journal (Dec. 1995) (http://dermatology.cdlib.org/DOJvol1num2/review/review-title.html), 12 pages.

Maibach, "Second-Generation Tetracyclines, A Dermatologic Overview: Clinical Uses and Pharmacology," *Cutis* (Nov. 1991) 48:411-417.

Margolis et al., "Antibiotic Treatment of Acne May Be Associated with Upper Respiratory Tract Infections," *Arch. Dermatol.* (Sep. 2005) 141:1132-1136.

Marks et al., "Comparative effectiveness of tetracycline and ampicillin in rosacea," *Lancet* (Nov. 13, 1971) 1049-1052.

Marks, R., "Concepts in the Pathogenesis of Rosacea", *Br. J. Derm.* (1968), 80, 170-177.

Marmion, V.J., "Tetracyclines in the Treatment of Ocular Rosacea," *Proc. Roy. Soc. Med.* (Jan. 1969) 62:11-12.

Marples et al., "Effects of Systemic Demethychlortetracycline on Human Cutaneous Microflora", *Applied Microbiology*, Aug. 1969, 18(2):228-234.

McAleer, M.A., et al., "The pathophysiology of rosacea," G. Ital. Dermatol. Venereol. 144:663-671 (2009).

McClellan, "Topical Metronidazole. A review of its use in rosacea," *Am. J. Clin. Dermatol.* (May-Jun. 2000) 1(3):191-199.

McGeehan et al., "Regulation of Tumour Necrosis Factor-Processing by a Metalloproteinase Inhibitor," *Nature* (Aug. 18, 1994) 370:558-561.

Merck Manual of Diagnosis and Therapy (Mark H. Beers, M.D. and Robert Berkow, M.D. eds.) (1999) 708-779 and 810-815.

Millar et al., "A general practice study investigating the effect of minocycline (Minocin) 50mg bd for 12 weeks in the treatment of acne vulgaris," *Br. J. Clin. Pract.* (Aug. 1987) 41(8):882-886.

Millikan, Larry M.D., "The proposed inflammatory pathophysiology of rosacea: Implications for treatment," Skinmed. 2:43-47 (Jan./Feb. 2003).

Miyachi et al., "Effects of Antibiotics on the Generation of Reactive Oxygen Species," *J. Invest. Dermatol.* (Apr. 1986) 86(4):449-453.

Murphy et al., "Oxytetracycline Treatment for Acne," *Lovelace Clinic Review* (Dec. 1962) 1(5):130-132.

Murrell et al., "Nitric Oxide: An Important Articular Free Radica,l" *JBJA J. Bone Joint Surg.* (Feb. 1996) 78-A(2):265-274.

Nanduri et al., "The Transcriptional Response of *Pasteurella multocida* to Three Classes of Antibiotics," *BMC Genomics* (2009) 10(Suppl. 2):S4, 10 pages.

Nicolaides et al., "Biorelevant Dissolution Testing to Predict the Plasma Profile of Lipophilic Drugs After Oral Administration," *Pharm. Res.* (2001) 18(3):380-388.

Nussler et al., "Inflammation, immunoregulation, and inducible nitric oxide synthase," *J. Leukocyte Biol.* (Aug. 1993) 54:171-178.

Palmer et al., "L-Arginine is the Physiological Precursor for the Formation of Nitric Oxide in Endothelium-Independent Relaxation," *Biochem. Biophys. Res. Comm.* (Jun. 30, 1988) 153(3):1251-1256.

Pechere et al., "Optimizing Economic Outcomes in Antibiotic Therapy of Patients With Acute Bacterial Exacerbations of Chronic Bronchitis," *J. Antimicrob. Chemother.* (2000) 45:19-24.

Periostat prescribing data, Rev. Nov. 2004, 2 pages.

Perlmutter, A., et al., "Oracea (doxycycline monohydrate)," Skinmed. 5(5):238-240 (Sep./Oct. 2006).

Perrella et al., "Suppression of Interleukin-1-Induced Nitric-Oxide Synthase Promoter/Enhancer Activity by Transforming Growth Factor-1 in Vascular Smooth Muscle Cells. Evidence for Mechanisms Other Than NF-B," *J. Biol. Chem.* (Jun. 7, 1996) 271(23):13776-13780.

Physicians' Desk Reference, 51st Edition, Monodox entry, pp. 1858-1860 (David W. Sifton, et al., eds. Medical Economics Company, Inc. 1997).

Physicians' Desk Reference, Periostat entry, pp. 944-946, and Table of Contents (54th Ed. 2000).

Pittner et al., "Endotoxin and TNF-Directly Stimulate Nitric Oxide Formation in Cultured Ra Hepatocytes, from Chronically Endotoxemic Rats," *Biochem. Biophys. Res. Comm.* (May 29, 1992) 185(1):430-435.

Plewig et al., "Double-Blind Study of Doxycycline in Acne Vulgaris", Archives of Dermatology, 101(4):435-438 (Jan.-Jun. 1970).

Plewig et al., *Acne: Morphogenesis and Treatment*, Springer-Verlag (1975) 261 and 297-301.

Quarterman, "Ocular Rosacea. Signs, symptoms and tea studies before and after treatment with doxycycline," *Arch. Dermatol.* (Jan. 1997) 133:49-54.

Rifkin et al., "Blocking Periodontal Disease Progression by Inhibiting Tissue-Destructive Enzymes: A Potential Therapeutic Role for Tetracyclines and Their Chemically Modified Analogs," *J. Periodontol.* (Aug. 1993, Supplement) 64(8):819-827.

Robbins et al., "Inducible Nitric Oxide Synthase is Increased in Murine Lung Epithelial cells by Cytokine Stimulation," *Biochem. Biophys. Res. Comm.* (Feb. 15, 1994) 198(3):835-843.

Roméro-Graillet, C., et al., Nitric oxide produced by ultraviolet-irradiated keratinocytes stimulates melanogenesis, J. Clin. Invest. 99(4):635-642 (1997).

Sainte-Marie et al., "Minocycline Modulation of Alpha-MSH Production by Karatinocytes in vitro," *Acta. Derm. Venereol.* (1999) 79:265-267.

Sakurai et al., "Nitric Oxide Production and Inducible Nitric Oxide Synthase Expression in Inflammatory Arthritides," *J. Clin. Invest.* (Nov. 1995) 96:2357-2363.

Sauermann, G., et al., "Influence of NO-synthase antagonists in rosacea patients," J. Invest. Dermatol. 108(4):657 (Apr. 1997), Abstract 718.
Savin et al., "Antibiotics and the Placebo Reaction in Acne," JAMA (Apr. 25, 1966) 196(4):153-155.
Savin, J.A., "The Bacteriology of Acne," Br. J. Derm. (1972) 86(Supp 8):3-9.
Schmidt et al., "Effect of Protein Binding on the Pharmacological Activity of Highly Bound Antibiotics," Antimicrob Agents Chemother (Nov. 2008) 52(11):3994-4000.
Schöpf et al., "Effects of Antimicrobial Agents on Leukocyte Locomotion and Chemotaxis," Cutan. Immunopathol. (1978) 80:437-452.
Schroeder et al., "Low Dose Doxycycline (LDD) Prevents Attachment Loss in Adult Periodontitis," J. Dent. Res. 71 (AADR Abstracts) (1992).
Schroeder et al., Low-Dose Tetracyclines (TCs) Decrease Elastane and B-Glucoronidase Activities in Gingival Crevicular Fluid (GCF), J. Dent. Res., 1990, 69:245, Abstract 1090.
Schwartz et al., "Doxycycline, Not Minocycline Induces Its own Resistance in Multidrug-Resistance, Community-Associated Methicillin-Resistant Staphylococcus aureus Clone USA300," Clin Infect Dis (May 15, 2009) 48:1483-1484.
Shapira et al., "Protection against Endotoxic Shock and Lipopolysaccharide-Induced Lo-cal Inflammation by Tetracycline: Crrelation with Inhibition of Cytokine Secretion", Infect. Immun., 64(3) (Mar. 1996), 825-828.
Skidmore et al., "Effects of Subantimicrobial-Dose Doxycycline in the Treatment of Moderate Acne," Arch. Dermatol. (Apr. 2003) 139:459-464.
Smith et al., "Tetracycline in Acne Vulgaris," Br. J. Derm. (1967) 79:78-84.
Sneddon, I.B.,"A Clinical Trial of Tetracycline in Rosacea," Br. J. Derm. (Dec. 1966) 78(12):649-652.
Sorsa et al., "Doxycycline in the Protection of Serum Alpha-1-Antitrypsin From Human Neutrophil Collagenase and Gelatinase," Antimicrob. Agents Chemother. (Mar. 1993) 37(3):592-594.
Stadler et al., "Articular Chondrocytes Synthesize Nitric Oxide in Response to Cytokines and Lipopolysaccharide," J. Immun. (Dec. 1, 1991) 147(11):3915-3920.
Stedman's Medical Dictionary 27th Edition, 2000, p. 394.
Stewart et al., "Mechanisms of antibiotic resistance in bacterial biofilms," Int J Med Microbiol (2002) 292(2):107-113.
Sugarman et al., "Off-Label Prescribing in the Treatment of Dermatologic Disease," Am. Acad. Derm. (Aug. 2002) 47(2):217-223.
Thiemermann et al., "Role of Tumour Necrosis Factor in the Induction of Nitric Oxide Synthase in a Rat Model of Endotoxin Shock," Br. J. Pharmacol. (1993) 110:177-182.
Thomas et al., "Long-Term Sub-Antimicrobial Doxycycline (Periostat®) as Adjunctive Management in Adult Periodontitis," Adv. Dent. Res. (Nov. 1998) 12:32-39.
Thomas, et al., "Long-term Use of Subantimicrobial Dose Doxycycline Does Not Lead to Changes in Antimicrobial Susceptibility," J Periodontal (Sep. 2000) 71(9):1472-1483.
Tilley et al., "Minocycline in Rheumatoid Arthritis," Ann. of Internal Med. (Jan. 15, 1995) 122(2):81-89.
Torresani, "Clarithromycin versus doxycycline in the treatment of rosacea," Int. J. Dermotol. (1997) 36:942-946.
Toyoda et al., "An Overview of Topical Antibiotics for Acne Treatment," Dermatology (1998) 196:130-134.
Tsuji et al., "Evaluation of daptomycin, telavancin, teicoplanin, and vancomycin activity in the presence of albumin or serum," Diagnostic Microbiol & Infect Dis (2008) 60:441-444.

Unkles et al., "Effect of Clindamycin, Erythomyci, Lincomycin, and Tetracycline on Growth and Extracellular Lipase Production by Propionibacteria in Vitro," Antimicrob. Agents Chemother. (Jan. 1982) 21(1):39-43.
Vernillo et al., "The Non-Antimicrobial Properties of Tetracycline for the Treatment of Periodontal Disease," Curr. Opin. Periodontol. (1994) 2:111-118.
Vogelman et al., "Kinetics of Antimicrobial Activity," J Pediatr (May 1986) 108:835-840.
Wahl et al., "Regulation of Chronic Inflammation," Mol. Path. Periodont. Dis. (1994) 183-190.
Walker et al., "An in vitro biofilm model of subgingival plaque," Oral Microbiol Immunol (2007) 22(3):152-161.
Walker et al., "Long-term Treatment with Sub-antimicrobial Dose Doxycycline Has No Antibacterial Effect on Intestinal Flora," J Clin Periodontal (2005) 32:1163-1169.
Walker et al., "Long-Term Treatment with Subantimicrobial Dose Doxycycline Exerts No Antibacterial Effect on the Subgingival Microflora Associated with Adult Periodontis," J Peridontal (Sep. 2000) 71:1465-1471.
Wassenaar, Trudy M., "Bacteria: More Than Pathogens," ActionBioscience.org (Jul. 2002), http://www.actionbioscience.org/biodiversity/wassenaar.html, 6 pages.
Webster et al, "Inhibition of Lipase Production in Propionibacterium Acnes by Sub-Minimal-Inhibitory Concentration of Tetracycline and Erythromycin," Br. J. Dermatol. (1981) 104:453-457.
Webster et al., "Inhibition of a Model of in Vitro Granuloma Formation by Tetracyclines and Ciprofloxacin," Arch. Dermatol. (Jun. 1994) 130:748-752.
Webster et al., "Mechanisms of Propionibacterium Acnes-Mediated Inflammation in Acne Vulgaris," Seminars in Derm. (Dec. 1982) 1(4):299-304.
Webster et al., "Suppression of Polymorphonuclear Leukocyte Chemotaclic Factor Production in Propionibacterium acnes by Sub-minimal Inhibitory Concentrations of Tetracycline, Amplicillin, Minocyclin, and Erythromycin," Antimicrob. Agents Chemother. (May 1982) 21(5):770-772.
Webster, "Inflammation in Acne Vulgaris," J. Am. Acad. Derm. (1995) 33:247-253.
Webster, G. F., "Acne," Curr. Probl. Dermatol. (Nov./Dec. 1996) 8(6):239-268.
Weller et al., "Nitric Oxide is Generated on the Skin Surface by Reduction of Sweat Nitrate," J. Invest. Dermatol. (1996) 107(3):327-31s.
Weller et al., "Nitric oxide: a key mediator in cutaneous physiology," Clinical and Experimental Dermatology, 2003, 28:511-514.
Wereide, "Long-Term Treatment of Rosacea With Oral Tetracycline" Acta. Derm. Venereol. (1969) 49:176-179.
Williams et al., "Absorption of doxycycline from a controlled release pellet formulation: The influence of food on bioavailability," Biopharmaceutics & Drug Disposition (1990) 11:93-105.
Witkowski et al., "Objective Evaluation of Demethylchlortetracycline Hydrochloride in the Treatment of Acne," JAMA (May 2, 1966) 196:111-114.
Yamasaki et al., "Increased Serine Protease Activity and Cathelicidin Promotes Skin Inflammation in Rosacea," Nat. Med. (Aug. 2007) 13(8):975-980.
Yamasaki et al., "The molecular pathology of rosacea," J. Derm. Sci. (2009) 55:77-81.
Zengin et al., "Meibomian Gland Dysfunction and Tear Film Abnormalities in Rosacea," Cornea (1995) 14:144-146.

* cited by examiner

Figure 1   Dissolution profile for doxycycline monohydrate IR beads

Figure 2  Dissolution profile for doxycycline monohydrate DR beads

Figure 3    Dissolution profile for doxycycline monohydrate composite capsules containing 75% IR and 25% DR beads Figure 4  Simulated steady state blood level profiles for various treatments Doxycycline
Steady State Study
Comparison of 75/25 IR/DR at Day 1 and at Steady State (Day 7)
(PK Curves from Mean Plasma Concentrations)

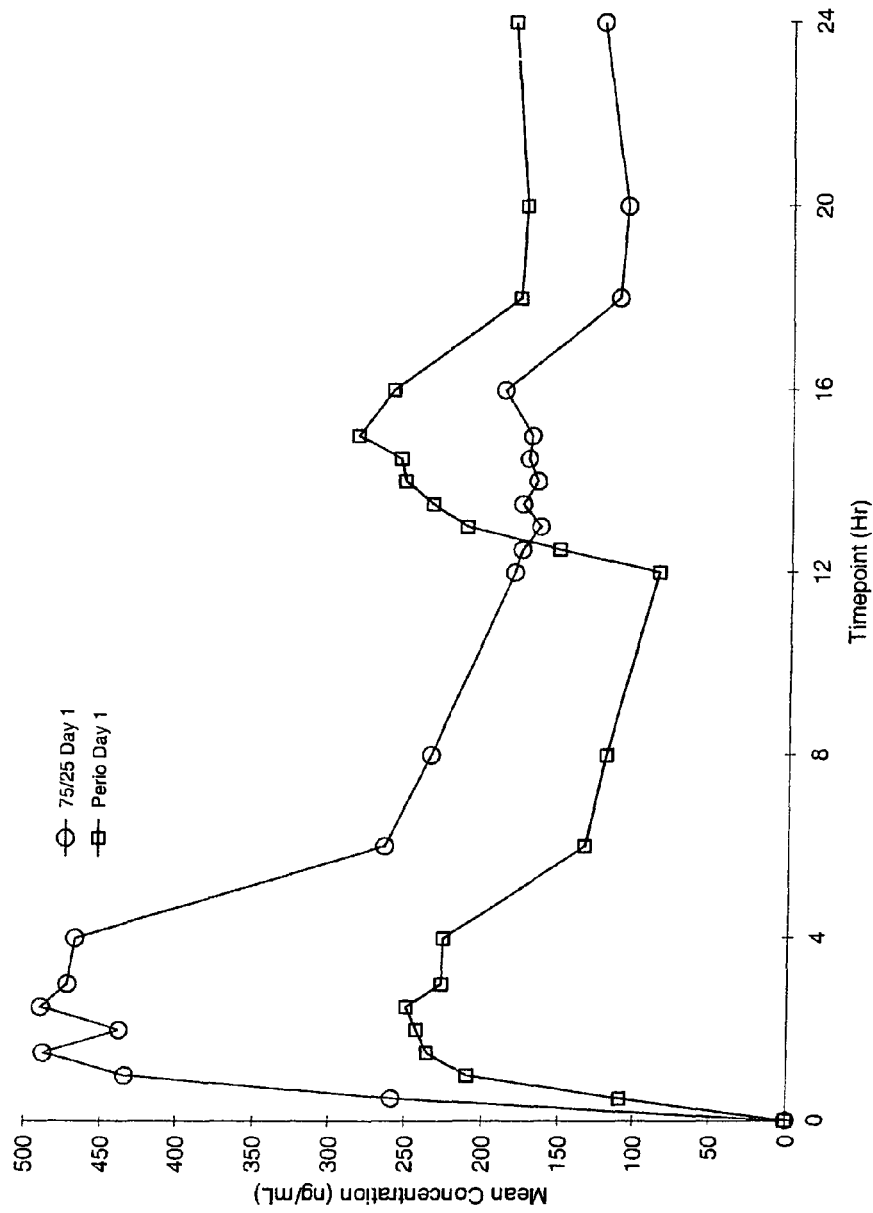

ONCE DAILY FORMULATIONS OF TETRACYCLINES

FIELD OF THE INVENTION

The present invention is concerned with once-daily compositions of tetracyclines, which can be used for the treatment of acute or chronic diseases, for instance those with inflammatory components. More specifically, the present invention is directed to a pharmaceutical composition of doxycycline for the treatment of diseases or conditions in which collagen destructive enzymes or molecules involved with such things as inflammation are contributing factors, and which is a once daily formulation. The compositions are especially useful for treating such common disease states as periodontal disease, rosacea, dry eye, acne and rheumatoid arthritis.

BACKGROUND OF THE INVENTION

Conventionally, doxycycline and related tetracyclines are used as broad spectrum antibiotics to treat various bacterial infections. Tetracyclines interfere with the protein synthesis of Gram positive and Gram-negative bacteria by preventing the binding of aminoacyl-tRNA to the ribosome. Their action is bacteriostatic (preventing growth of bacteria) rather than killing (bactericidal). The doses commonly used for doxycycline to achieve the antibiotic effect are 100 mg and 50 mg.

Doxycycline, as well as other tetracyclines, also has other therapeutic uses in addition to its antibiotic properties. For example, doxycycline is known to inhibit the activity of collagen destruction enzymes such as collagenase, gelatinase, and elastase. Its collagenase inhibition activity has been used to treat periodontal disease. For another example, doxycycline can inhibit lipase produced by the bacterium P. acnes and thus reduces the availability of free fatty acids that are involved in inflammation. Doxycycline may also reduce inflammation by reducing cytokine levels so that the integrity of the follicular wall is preserved. Thus, doxycycline also has the potential in treating skin diseases, such as acne.

Investigators have found that sub-antimicrobial doses of tetracyclines are useful in the treatment of various ailments, although the mechanisms responsible for the effects are not entirely clear. For instance, U.S. Pat. No. 6,455,583 discloses treating meibomian gland disease by oral administration of non-antimicrobial amounts of a tetracycline to the patient. U.S. Pat. No. 6,100,248 teaches a method of inhibiting cancer growth by administering tetracyclines which have been chemically modified to attenuate or delete their antibacterial activity. Methods to reduce collagenolytic enzymes by administration of amounts of a tetracycline that are generally lower than the normal amounts used for antimicrobial therapy are disclosed in U.S. Pat. No. 4,666,897. The patents cited in this paragraph are hereby incorporated herein by reference.

In the market, there are two implantable products for site-specific use in the treatment of periodontal disease. The PerioChip® is a small, orange-brown chip, which is inserted into periodontal pockets. Each PerioChip® contains 2.5 mg of chlorhexidine gluconate in a biodegradable, resorbable matrix. It is recommended that PerioChip® treatment be administered once every three months in pockets that remain at 5 mm or deeper. A second product, Atridox®, is an injectable, resorbable gel, which provides the subgingival controlled-release of 42.5 mg doxycycline for approximately one week. Additionally, there is now available a new oral medication called Periostat®, which delivers 20 mg doxycycline systemically as a collagenase inhibitor used in patients with adult periodontal disease. Most people would prefer to take a pill to the implant. However, Periostat® requires twice daily dosing and raises concerns about patient compliance. Thus, it would be highly beneficial to develop a once-a-day formulation for doxycycline.

While doxycycline is generally effective for treating infection, the use of doxycycline can lead to undesirable side effects. For example, the long-term administration of the antibiotic doxycycline can reduce or eliminate healthy biotic flora, such as intestinal flora, and can lead to the production of antibiotic resistance organisms or the overgrowth of yeast and fungi. Because of the undesirable side effects from its antibiotic properties, there is a need for a unique dose and an improved formulation to deliver doxycycline such that the anti-collagen destructive enzymes or other such beneficial effect of tetracyclines, especially doxycycline, is attained, but antibacterial effects are avoided.

SUMMARY OF THE INVENTION

The present invention is in its broadest sense directed to pharmaceutical compositions of tetracyclines designed to provide an extended release profile in vivo of levels of active ingredient that at steady state are high enough to be effective to have a beneficial effect in the treatment of a disease or condition, but not as high as to exert an antibacterial effect. Such pharmaceutical compositions are formulated into dosage forms that can be taken once a day. One object of the present invention is to provide a pharmaceutical composition of doxycycline, which can be given once a day yet meet the steady state blood levels required for the treatment or prevention of diseases or conditions caused by overproduction of collagenase, such as periodontal disease, or other biochemicals associated with certain disease states which could be regulated with doxycycline, such as conditions involving inflammation, without the undesirable effects of long term antibiotic activity.

One object of the present invention is to provide a once-daily pharmaceutical composition containing doxycycline that will give steady state blood levels of doxycycline of a minimum of about 0.1 µg/ml and a maximum of about 1.0 µg/ml.

In one aspect of the invention is an immediate release formulation of doxycycline containing less than 50 mg but more than 25 mg, preferably about 40 mg. doxycycline base.

In another aspect, the invention is directed to a pharmaceutical composition of doxycycline that contains an immediate release (IR) component of the drug and a delayed release (DR) component of the drug, which are combined into one dosage unit for once-daily dosing. The components can be present in various ratios, although preferred are ratios of about 70:30 to about 80:20, and most preferred 75:25, IR:DR, with the total dosage of doxycycline being less than about 50 mg. and preferably about 40 mg. The ratio refers to the dose breakdown between IR and DR, e.g., 80:20 means 80% of 40 mg is from IR portion and 20% of 40 mg is from DR portion.

Yet another object of the invention is to provide a method for treating diseases or conditions in which collagenase is produced in excessive amounts causing pathological destruction of tissues, such as periodontal disease, rheumatoid arthritis, hyperparathyroidism, diabetes and acne, by administering the once-daily dosage of doxycycline. See, e.g., U.S. Pat. No. 4,666,897 of Golub.

Another object of the present invention is to provide a method for systemic treatment of rosacea, a dermatological condition of humans, by administering the once-daily dosage of doxycycline according to the present invention.

Another object of the invention is to provide processes for preparing the once-daily compositions of the present invention.

BRIEF DESCRIPTION OF THE DRAWINGS

FIG. 6 compares the pharmacokinetic curves of 75:25 IR:DR (40 mg.) formulation with the Periostat® 20 mg. twice daily dosage form.

DETAILED DESCRIPTION OF THE INVENTION

Figure 1:
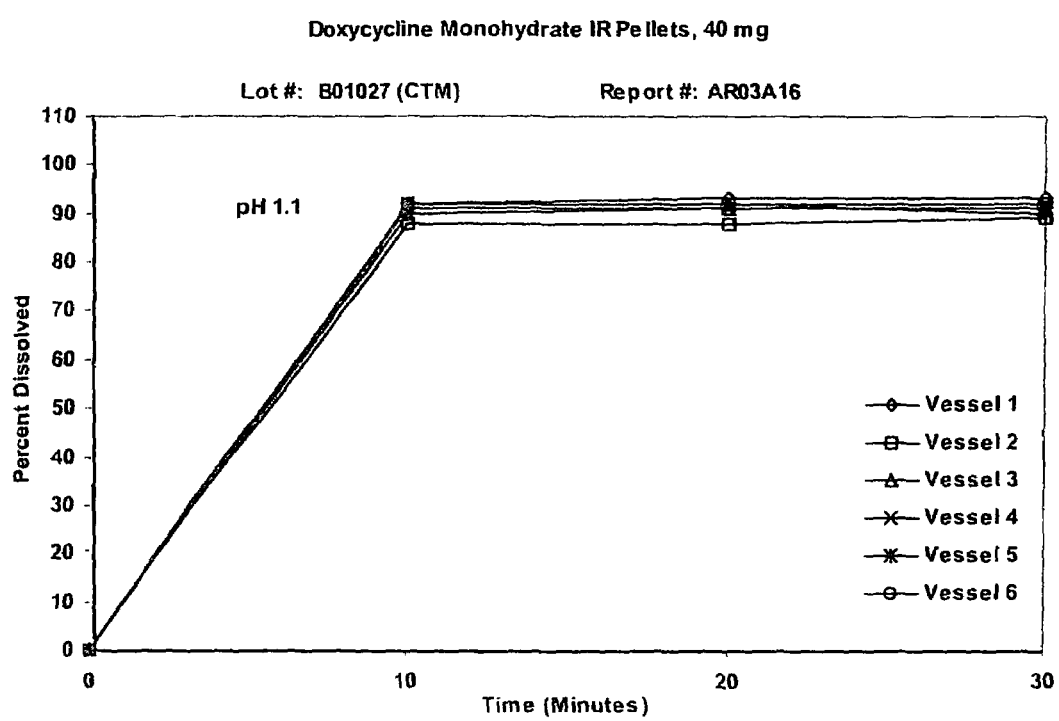
FIG. 1 shows dissolution profiles for doxycycline monohydrate immediate-release beads within the scope of the present invention, which were determined by utilizing a computer algorithm that is based on a compartmental absorption and transit model to deconvolute in vivo release profiles from in vivo human plasma data. The in silico model was first validated and tested using human plasma data from immediate release dosage forms.

While the following description is directed primarily to doxycycline, it is contemplated that the present invention is applicable to other tetracyclines, particularly other tetracyclines that have similar in vivo absorption profiles as doxycycline, more specifically tetracyclines that have a similar region of absorption in the gastrointestinal tract as doxycycline. Different kinds of tetracyclines and the beneficial effects on various disease states are disclosed in, for example, WO 02/083106 and U.S. Pat. No. 6,638,922, each of which are incorporated in their entireties herein by reference.

The present invention can be accomplished by providing an orally administered composition of, as an example, doxycycline which is designed to provide certain steady state blood levels of the drug, while in a formulation that requires that the mammal, preferably human, to take only one dosage a day. The compositions of the present invention are intended to be useful in lieu of multiple daily dosing, such as twice-daily dosing, of compositions that achieve the same effects. The preferred blood level of doxycycline, or other tetracyclines of comparable physiological and absorption properties, is between about 0.1 and about 1.0 µg/ml at the steady state. Preferably, the blood levels stay within the preferred blood level, with daily dosing, for the entire course of treatment. More preferably, the blood levels are between about 0.3 µg/ml and about 0.8 µg/ml.

The above blood serum levels allow for the desired anti-collagenase and anti-inflammatory activity of doxycycline, without being accompanied by undesirable antibiotic activity. It was surprisingly found that these levels can be accomplished with a single daily dose of an immediate release formulation containing below 50 mg. but more than 25 mg., preferably about 40 mg. doxycycline base.

"About" means within the pharmaceutically acceptable limits found in the United States Pharmacopia (USP-NF 21), 2003 Annual Edition, or available at www.usp.org, for amount of active pharmaceutical ingredients. With respect to blood levels, "about" means within FDA acceptable guidelines.

By "immediate release" formulation is meant a dosage form that is intended to release substantially all of the active ingredient on administration with no enhanced, delayed or extended release effect. Such a composition of doxycycline can be in the form of a liquid suspension or solution, or as a solid such as a tablet, pellet (used interchangeably with bead or beadlet herein), particle, capsule or gel. Preferred in the present invention are tablets, or beadlets in a capsule.

As pharmaceutically active ingredients, any form of the tetracycline compound can be used provided it will comply with the required blood serum levels of the present invention. Doxycycline, for instance, is commonly used in pharmaceutical formulations under two chemical forms: the monohydrate form and the hyclate form. The monohydrate is the base molecule hydrated with one molecule of water and is used in the formulation of capsules and, in some markets, powder oral suspensions (to be reconstituted with water). The hyclate is a hydrochloric acid salt solvated with water and ethanol and is typically used in the formulation of capsules or tablets. The amount of doxycycline in the compositions of the present invention refers to doxycycline base. Also, in the compositions of the present invention there may be more than one active ingredient. That is, the doxycycline can be combined with another therapeutic or nutritional substance in the dosage forms.

Immediate Release Dosage Forms

There are many ways known in the art to formulate such immediate release dosage forms. For instance, an immediate release tablet can be prepared by mixing doxycycline with a bulking agent such as microcrystalline cellulose, for example, AVICEL® (FMC Corp.) or EMCOCEL® (Mendell Inc.); dicalcium phosphate, for example, EMCOMPRESS® (Mendell Inc.); calcium sulfate, for example, COMPACTROL® (Mendell Inc.); and starches, for example, STARCH 1500. Additionally, one can add a disintegrating agent, such as microcrystalline cellulose, starches, crospovidone, for example, POLYPLASDONE XL® (International Specialty Products); sodium starch glycolate, for example, EXPLOTAB® (Mendell Inc.); and croscarmellose sodium, for example, AC-DI-SOL® (FMC Corp.). Antiadherants and glidants employed herein can include talc, cornstarch, silicon dioxide, sodium lauryl sulfate, colloidal silica dioxide, and metallic stearates.

Lubricants may be employed, such as magnesium stearate, calcium stearate, sodium stearate, stearic acid, sodium stearyl fumarate, sterotex, talc, waxes and the like. Binding agents may be employed, such as polyvinyl pyrollidone, starch, methylcellulose, hydroxypropyl methylcellulose, carboxymethyl cellulose, and the like.

The present invention is preferably formulated into a tablet prepared using methods known in the art, including a wet granulation method and a direct compression method. The oral tablets are prepared using any suitable process known to the art. See, for example, Remington's Pharmaceutical Sciences, 18$^{th}$ Edition, A. Gennaro, Ed., Mack Pub. Co. (Easton, Pa. 1990), Chapters 88-91, the entirety of which is hereby incorporated by reference. Typically, the active ingredient, doxycycline, is mixed with pharmaceutically acceptable excipients (e.g., the binders, lubricants, etc. listed above) and compressed into tablets. Preferably, the dosage form is prepared by a wet granulation technique or a direct compression method to form uniform granulates. Alternatively, the active ingredient(s) can be mixed with the granulate after the granulate is prepared. The moist granulated mass is then dried and sized using a suitable screening device to provide a powder, which can then be filled into capsules or compressed into matrix tablets or caplets, as desired.

In a preferred embodiment, the tablets are prepared using the direct compression method. The direct compression method offers a number of potential advantages over a wet granulation method, particularly with respect to the relative ease of manufacture. In the direct compression method, at least one pharmaceutically active agent and the excipients or other ingredients are sieved through a stainless steel screen, such as a 40 mesh steel screen. The sieved materials are then charged to a suitable blender and blended for 10 minutes with an intensifier bar for three minutes. The blend is then compressed into tablets on a rotary press using appropriate tooling.

As mentioned above, another preferred dosage form for the immediate release composition is a capsule containing immediate release beadlets or pellets. Methods for making such pellets are set forth in the section below (i.e., the IR pellets). The pellets are filled into capsules, for instance gelatin capsules, by conventional techniques.

Combination IR/DR Dosage Forms

In another embodiment of the present invention is a composition having a substantially immediate release dose of doxycycline, followed by at least one additional dose at a predetermined time, in a unit dosage. The first immediate release dose of the composition can be in the form of powder, granule, beadlet, or tablet; the second delayed-release portion can be coated granular, coated beadlet, coated tablet, or uncoated matrix tablet. The ratio between the immediate-release portion, or component, and the delayed-release portion, or component, can be used to adjust the in vitro drug release profile and in vivo blood concentration profile. By providing such a drug release profile, the compositions eliminate the need for a second dose for the day. Additionally, the total dose of doxycycline is below 50 mg. to avoid the undesirable side effects from its antibiotic properties, but more than 25 mg. to achieve the anti-collagenase and/or anti-inflammatory effect.

Several dosage form variations can be used to achieve a product with these attributes. For example, an immediate-release powder blend can be encapsulated with a delayed-release tablet or delayed-release pellets. A further example is an immediate-release tablet and a delayed-release tablet that are prepared separately and encapsulated into an appropriate sized capsule shell. Or, for example, a delayed-release tablet can be used as a core and the immediate-release portion can be compressed as an outer layer using a press coater or overcoated using a drug layering technique, both techniques of which can be found in Gunsel and Dusel, Chapter 5, "Compression-coated and layer tablets", in Pharmaceutical Dosage Forms:Tablets, Second Edition, Volume 1, Edited by H. A. Lieberman, L. Lachman, and J. B. Schwartz, Marcel Dekker, Inc. New York and Basel (1990).

Multiparticulate Capsules

As a preferred embodiment, the IR/DR composition of doxycycline is in the form of a capsule containing beadlets. At present, it is preferred to have two different types of units in a single form multiple-unit dosage form.

The first unit is an immediate release dosage form, preferably in pellet form. This component can also be a powder if desired or necessary. In either case, the dosage form may have a surface-active agent such as sodium lauryl sulfate, sodium monoglycerate, sorbitan monooleate, polyoxyethylene sorbitan monooleate, glyceryl monostearate, glyceryl monooleate, glyceryl monobutyrate, any one of the Pluronic line of surface-active polymers, or any other suitable material with surface active properties or any combination of the above. Preferably, the surface-active agent would be a combination of sodium monoglycerate and sodium lauryl sulfate. The concentration of these materials in this component can range from about 0.05 to about 10.0% (W//W).

Other excipient materials that can be employed in making drug-containing pellets are any of those commonly used in pharmaceutics and should be selected on the basis of compatibility with the active drug and the physicochemical properties of the pellets. These include, for instance: binders such as cellulose derivatives such as methylcellulose, hydroxyethyl cellulose, hydroxypropyl cellulose, hydroxypropyl methylcellulose, polyvinylpyrrolidone, polyvinylpyrrolidone/vinyl acetate copolymer and the like; disintegration agents such as cornstarch, pregelatinized starch, cross-linked carboxymethylcellulose (AC-DI-SOL®), sodium starch glycolate (EXPLOTAB®), cross-linked polyvinylpyrrolidone (PLASDONE® XL), and any disintegration agents used in tablet preparations, which are generally employed in immediate release dosages such as the one of the present invention; filling agents such as lactose, calcium carbonate, calcium phosphate, calcium sulfate, microcrystalline cellulose, dextran, starches, sucrose, xylitol, lactitol, mannitol, sorbitol, sodium chloride, polyethylene glycol, and the like; surfactants such as sodium lauryl sulfate, sorbitan monooleate, polyoxyethylene sorbitan monooleate, bile salts, glyceryl monostearate, the PLURONIC® line (BASF), and the like; solubilizers such as citric acid, succinic acid, fumaric acid, malic acid, tartaric acid, maleic acid, glutaric acid sodium bicarbonate and sodium carbonate and the like; and stabilizers such as any antioxidation agents, buffers, acids, and the like, can also be utilized.

The pellet can be made by, for example, simple granulation, followed by sieving; extrusion and marumerization; rotogranulation; or any agglomeration process that results in a pellet of reasonable size and robustness. For extrusion and marumerization, the drug and other additives are granulated by addition of a binder solution. The wet mass is passed through an extruder equipped with a certain size screen, and the extrudates are spheronized in a marumerizer. The resulting pellets are dried and sieved for further applications. One may also use high-shear granulation, wherein the drug and other additives are dry-mixed and then the mixture is wetted by addition of a binder solution in a high shear-granulator/mixer. The granules are kneaded after wetting by the combined actions of mixing and milling. The resulting granules or pellets are dried and sieved for further applications.

As stated earlier, it is also possible to have this immediate release component as a powder, although the preferred form is a pellet due to mixing and de-mixing considerations.

Alternatively, the immediate release beadlets or pellets of the composition can be prepared by solution or suspension layering, whereby a drug solution or dispersion, with or without a binder, is sprayed onto a core or starting seed (either prepared or a commercially available product) in a fluid bed processor or other suitable equipment. The cores or starting seeds can be, for example, sugar spheres or spheres made from microcrystalline cellulose. The drug thus is coated on the surface of the starting seeds. The drug-loaded pellets are dried for further applications.

The second unit should have a delayed release (DR) profile, and needs to be able to address the changing pH of the GI tract, and its effect on the absorption of doxycycline or other tetracycline. This pellet should have all of the ingredients as mentioned for the first unit pellet, as well as optionally some organic acid that will be useful to reduce the pH of the microenvironment of the pellet, and thus facilitate dissolution. These materials are, but not limited to, citric acid, lactic acid, tartaric acid, or other suitable organic acids. These materials should be present in concentrations of from about 0 to about 15.0% (w/w); preferably these materials would be present in concentrations of from about 5.0 to about 10.0 percent (w/w). The process for manufacturing these pellets is consistent with the process described above for the first unit pellet.

Unlike the first unit pellet, the second unit delayed-release component has a controlling coat applied to the surface of the pellet such that the release of the drug from the pellet is delayed. This is accomplished by applying a coating of enteric materials. "Enteric materials" are polymers that are substantially insoluble in the acidic environment of the stomach, but are predominantly soluble in intestinal fluids at specific pHs. The enteric materials are non-toxic, pharmaceutically acceptable polymers, and include, for example, cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e.g., EUDRAGIT® L30D55, EUDRAGIT® FS30D, EUDRAGIT® L100, KOLLICOAT® EMM30D, ESTACRYL® 30D, COATERIC®, and AQUATERIC®). The foregoing is a list of possible materials, but one of skill in the art would recognize that it is not comprehensive and that there are other enteric materials that would meet the objectives of the present invention of providing for a delayed release profile. These coating materials can be employed in coating the surfaces in a range of from about 1.0% (w/w) to about 50% (w/w) of the pellet composition. Preferably these coating materials should be in a range of from about 20 to about 40 percent (w/w). The pellets may be coated in a fluidized bed apparatus or pan coating, for example.

With the enteric coated pellets, there is no substantial release of doxycycline in the acidic stomach environment of approximately below pH 4.5. The doxycycline becomes available when the pH-sensitive layer dissolves at the greater pH of the small intestine; after a certain delayed time; or after the unit passes through the stomach. The preferred delay time is in the range of two to six hours.

As a variation of this embodiment, the DR pellet contains layers of the doxycycline, separated by protective layers, and finally an enteric coating, resulting in a "repeat-action" dosage delivery. Such a dosage form may meet the blood level requirements of the release profile of the present invention if the release of the doxycycline, or other tetracycline, in all of the layers is within the absorption window for the drug.

An overcoating layer can further optionally be applied to the IR/DR pellets of the present invention. OPADRY®, OPADRY II® (Colorcon) and corresponding color and colorless grades from Colorcon can be used to protect the pellets from being tacky and provide colors to the product. The suggested levels of protective or color coating are from 1 to 6%, preferably 2-3% (w/w).

Many ingredients can be incorporated into the overcoating formula, for example to improve the coating process and product attributes, such as plasticizers: acetyltriethyl citrate, triethyl citrate, acetyltributyl citrate, dibutylsebacate, triacetin, polyethylene glycols, propylene glycol and others; lubricants: talc, colloidal silica dioxide, magnesium stearate, calcium stearate, titanium dioxide, magnesium silicate, and the like.

The delayed release and immediate release units are combined in the dosage form (in this instance, the different pellets are put into capsules) in a predetermined ratio, preferably about 70:30 to about 80:20, most preferably 75:25 (IR/DR), which will achieve the desired steady state blood serum levels with only once-daily dosing.

The composition, preferably in beadlet form, can be incorporated into hard gelatin capsules, either with additional excipients, or alone. Typical excipients to be added to a capsule formulation include, but are not limited to: fillers such as microcrystalline cellulose, soy polysaccharides, calcium phosphate dihydrate, calcium sulfate, lactose, sucrose, sorbitol, or any other inert filler. In addition, there can be flow aids such as fumed silicon dioxide, silica gel, magnesium stearate, calcium stearate or any other material imparting flow to powders. A lubricant can further be added if necessary by using polyethylene glycol, leucine, glyceryl behenate, magnesium stearate or calcium stearate.

The composition may also be incorporated into a tablet, in particular by incorporation into a tablet matrix, which rapidly disperses the particles after ingestion. In order to incorporate these particles into such a tablet, a filler/binder must be added to a table that can accept the particles, but will not allow their destruction during the tableting process. Materials that are suitable for this purpose include, but are not limited to, microcrystalline cellulose (AVICEL®), soy polysaccharide (EM-COSOY®), pre-gelatinized starches (STARCH® 1500, NATIONAL® 1551), and polyethylene glycols (CARBOWAX®). The materials should be present in the range of 5-75% (w/w), with a preferred range of 25-50% (w/w).

In addition, disintegrants are added in order to disperse the beads once the tablet is ingested. Suitable disintegrants include, but are not limited to: cross-linked sodium carboxymethyl cellulose (AC-DI-SOL®), sodium starch glycolate (EXPLOTAB®, PRIMOJEL®), and cross-linked polyvinylpolypyrrolidone (Plasone-XL). These materials should be present in the rate of 3-15% (w/w), with a preferred range of 5-10% (w/w).

Lubricants are also added to assure proper tableting, and these can include, but are not limited to: magnesium stearate, calcium stearate, stearic acid, polyethylene glycol, leucine, glyceryl behenate, and hydrogenated vegetable oil. These lubricants should be present in amounts from 0.1-10% (w/w), with a preferred range of 0.3-3.0% (w/w).

Tablets are formed, for example, as follows. The particles are introduced into a blender along with AVICEL®, disintegrants and lubricant, mixed for a set number of minutes to provide a homogeneous blend which is then put in the hopper of a tablet press with which tablets are compressed. The compression force used is adequate to form a tablet; however, not sufficient to fracture the beads or coatings.

It will be appreciated that the multiple dosage forms of the present invention can deliver dosages of pharmaceutically active doxycycline, or other tetracycline, to achieve the desired levels of the drug in a recipient over the course of about 24 hours at steady state with a single daily oral administration.

The present invention also provides a method for treating a mammal with doxycycline, or other tetracycline. The method involves administering a doxycycline, or other tetracycline, composition according to the present invention to a mammal, preferably a human, in need of the anti-collagenase or anti-inflammatory activity of doxycycline or other tetracycline substantially without accompanying antibiotic activity. Systemic administration is preferred, and oral administration is most preferred.

Using the compositions of the present invention, the steady state blood levels of doxycycline or other tetracycline of a minimum of about 0.1 μg/ml, preferably about 0.3 μg/ml and a maximum of about 1.0 μg/ml, more preferably about 0.8 μg/ml, can be achieved to treat diseases with increased collagenase production, such as periodontal, skin diseases and the like, as well as inflammatory states. Indeed, any disease state treatable with sub-antimicrobial blood levels of a tetracycline given in multiple daily dosages can also be treated using the corresponding once-daily formulations of the present invention.

The invention will now be illustrated by the following examples, which are not to be taken as limiting.

EXAMPLES

Example 1

Preparation of Layered IR Pellets Containing Doxycycline Monohydrate

A dispersion of doxycycline monohydrate was prepared as follows: To 5.725 kilograms of deionized water were added 0.113 kilogram hydroxypropyl methylcellulose and 1.5 kilograms of doxycycline monohydrate, followed by moderate mixing, using a stirring paddle for 30 minutes. The drug dispersion was sprayed onto sugar seeds (30/35 mesh) in a 9" Wurster Column of a GPCG-15 fluid bed processor. Until the entire dispersion was applied, the pellets were dried in the column for 5 minutes. The drug-loaded pellets were discharged from the Wurster Column and passed through a 20 mesh screen. A protective coat (e.g., OPADRY® beige) also can be applied onto the IR beads to provide color or physical protection. FIG. 1 shows a typical dissolution profile for doxycycline monohydrate immediate-release beads.

Example 2

Preparation of Enteric Coated Pellets Containing Doxycycline Monohydrate

Figure 2:
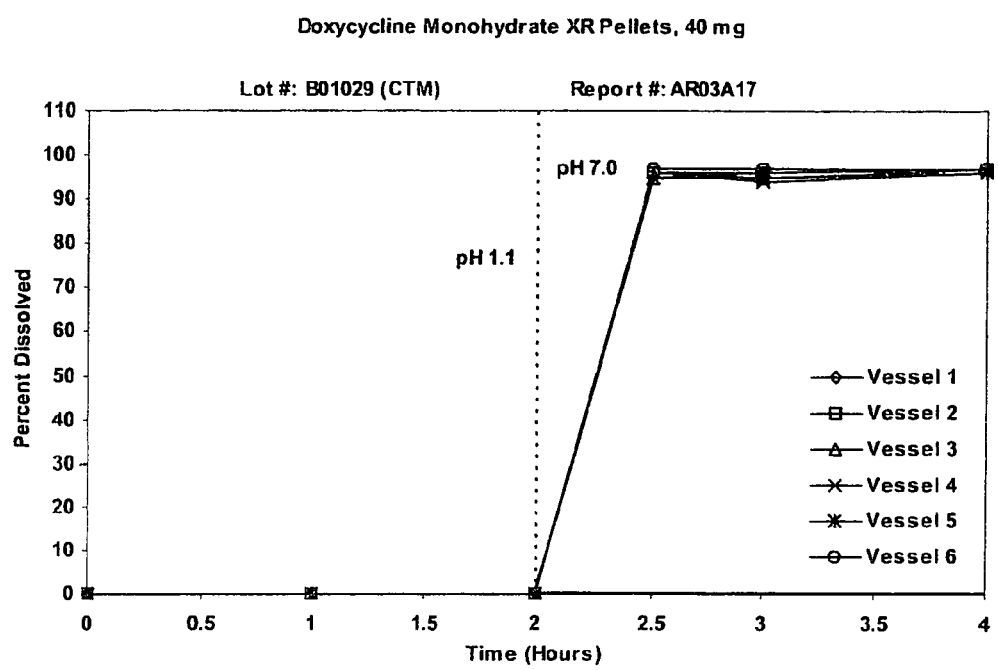
FIG. 2 shows in silico dissolution profiles for doxycycline monohydrate delayed-release beads.

The EUDRAGIT® L30D55 coating dispersion was prepared by adding 0.127 kilogram of triethyl citrate into 3.538 kilograms of EUDRAGIT® L30D55 (solid content: 1.061 kilograms) and stirring for at least 30 minutes. Talc 0.315 kilogram was dispersed into 2.939 kilograms of deionized water. The plasticized EUDRAGIT® L30D55 was combined with the talc dispersion and screened through a 60 mesh screen. The resulting combined dispersion was sprayed onto drug-loaded pellets (3.5 kilograms) prepared according to Example 1 in a 9" Wurster Column of a GPCG-15 fluid bed processor. A protective coat (e.g., OPADRY® beige) may be applied onto the DR beads to provide color or physical protection. FIG. 2 shows a typical dissolution profile for doxycycline monohydrate delayed-release beads.

Example 3

Encapsulation of Drug-Loaded Pellets and Enteric Coated Pellets

Figure 3:
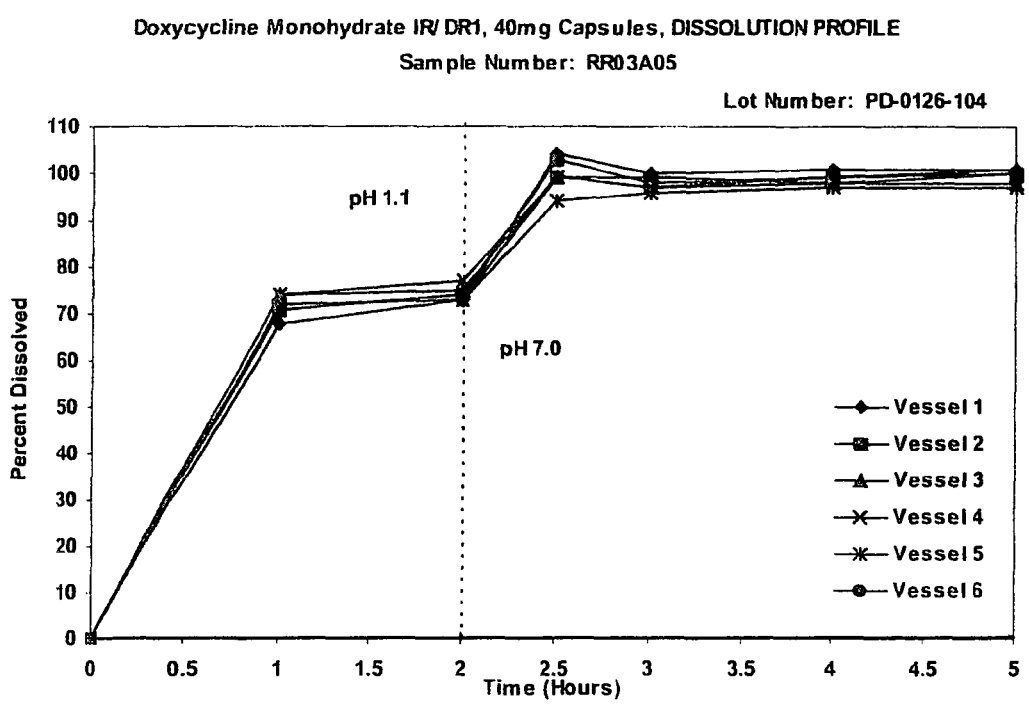
FIG. 3 shows in silico dissolution profiles for the composite capsules with 75% of immediate-release beads and 25% of delayed-release beads.

Capsules can be prepared by filling the drug-loaded pellets and enteric coated pellets individually into appropriate sized capsule shells. The ratio between the drug-loaded pellets and enteric-coated pellets can be 100:0 to 70:30. For example, at the ratio of 75:25, the fill weight of drug-loaded pellets can be calculated based on the actual potency of the drug-loaded pellets to deliver 30 mg doxycycline; the fill weight of enteric-coated pellets also can be calculated based on the actual potency of the enteric-coated pellets to deliver 10 mg doxycycline. Romoco CD5 or MG-2 pellet filling machine can be used to accurately fill the pellets into the desired capsule shells. FIG. 3 shows the typical dissolution profile for the composite capsules with 75% of immediate-release beads and 25% of delayed-release beads.

Example 4

Preparation of Delayed Tablet Containing Doxycycline Monohydrate

Doxycycline monohydrate 0.5625 kilogram was blended with 3.15 kilograms of microcrystalline cellulose in a V-shaped blender for 15 minutes and the powder blend was lubricated with magnesium stearate (0.0375 kilogram) for additional 5 minutes. Doxycycline monohydrate (0.2 kilogram) was granulated with EUDRAGIT® L100 powder (1.280 kilograms) and microcrystalline cellulose powder (0.5 kilograms) using isopropyl alcohol as a granulating fluid. The wet granulation was dried in a fluid bed dryer and the dried granulations were blended with magnesium stearate (0.020 kilogram) in a V-shaped blender for 5 minutes. Doxycycline powder blend and granulation were put on a belayed tablet press to compress into a belayed tablet with target weights of 200 mg and 100 mg for the powder blend and granulation layers, respectively.

Example 5

Preparation of Immediate-Release Tablet Containing Doxycycline monohydrate

Doxycycline monohydrate 1.0 kilogram was blended with 2.225 kilogram of microcrystalline cellulose (AVICEL® PH 102) in a V-shaped blender for 5 minutes. The remaining microcrystalline cellulose (1.75 kilogram of AVICEL® PH 202) is then added to the powder blend in the V-shaped blender and mixed for additional 30 minutes. The powder blend was then lubricated with magnesium stearate (0.025 kilogram) for 5 minutes. The lubricated powder blend was compressed into a tablet with the target weight of 200 mg. The tablets can be further coated with a polymeric protective layer.

Example 6

Figure 4:
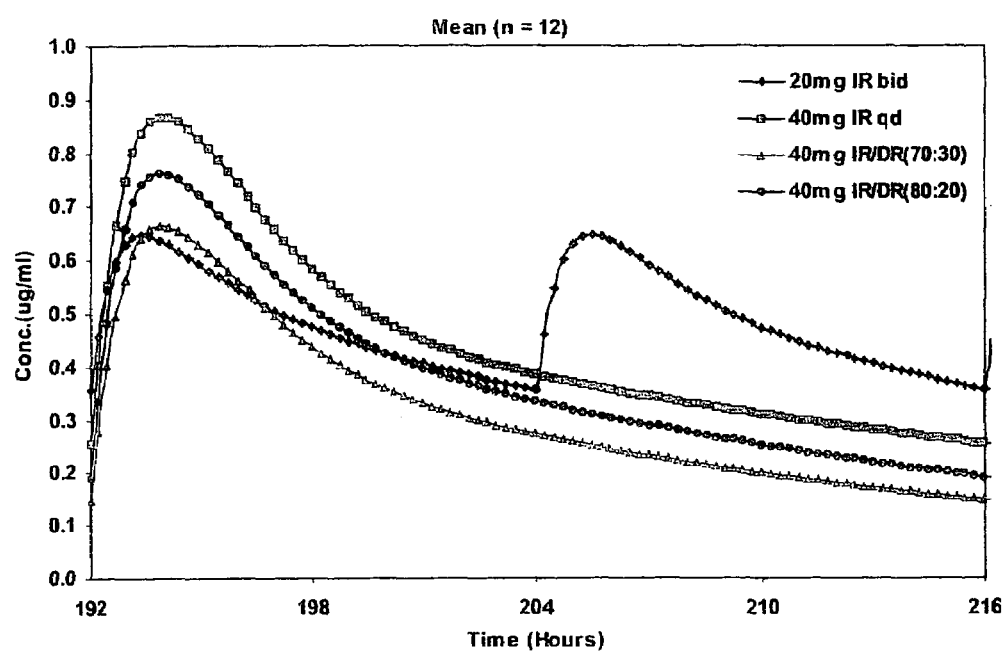
FIG. 4 shows predicted blood levels vs. time profiles at steady state for various treatments (i.e., 40 mg once-a-day IR formula, 40 mg once-a-day IR and DR combinations at 70:30 and 80:20 ratios, and twice-a-day 20 mg doxycycline treatment).

The simulated blood levels-time profiles at steady state for various treatments (e.g., 40 mg once-a-day IR formula, 40 mg once-a-day IR and DR combinations at 70:30 and 80:20 ratios, and twice-a-day 20 mg doxycycline treatment) were determined by in silico modeling, and are shown in FIG. 4. Using the unique dose (i.e., <50 mg, preferably 40 mg) and composition (IR beads or IR/DR combinations), the steady state blood levels of doxycycline of a minimum of about 0.1 ug/ml, preferably about 0.3 ug/ml and a maximum of about 1.0 ug/ml, more preferably about 0.8 ug/ml, can be achieved to treat such conditions as periodontal and skin diseases.

Example 7

Size 0 capsules containing a ratio of 75:25 of drug-loaded IR pellets to enteric coated DR pellets were prepared as follows. The IR and DR pellets were prepared as set forth in Examples 1 and 2. From the assay value of the doxycycline used to make the pellets, it was determined that 41.26 mg potency of the capsules would correspond to an actual strength of 40 mg. doxycycline. The potency of the IR pellets was 194 mg doxycycline per gram of pellets (mg/g), and for the DR pellets was 133 mg/g. Accordingly, it was calculated that for each capsule the fill weight of IR beads would be 159.5 mg, and for DR beads 77.6 mg, corresponding to 75:25 of IR:DR of a 40 mg capsule.

Example 8

A pharmacokinetic (PK) study was conducted in human subjects to compare a first group taking the extended release doxycycline capsule (see Example 7) (75/25 IR/DR 40 mg) administered orally once daily versus a second group taking Periostat® tablets (20 mg) administered orally twice daily, twelve hours apart.

Pharmacokinetic blood draws were collected on Nominal Study Day 1 for first and second groups, and on Day 7 for the first group as follows: 0 (pre dose), 0.5, 1, 1.5, 2, 2.5, 3, 4, 6, 8, 12 (before the post-morning dose, if applicable), 12.5, 13, 13.5, 14, 14.5, 15, 16, 18, 20, and 24 hours after the morning dose.

The data from this study were shown in the following Table 1.

TABLE 1

|  | 75/25 IR/DR Day 1 | 75/25 IR/DR Day 7 steady state | Periostat ® Day 1 |
| --- | --- | --- | --- |
| $T_{max}$ | 2.2 | 2.3 | 1.9/11.9 |
| $C_{max}$ | 562 | 602 | 100/333 |
| $AUC_{0-24}$(Hr*ng/ml) | 5388 | 7230 | 4280 |

Mean $C_{max}$ at Day 1 from the 75/25 IR/DR 40 mg capsules is comparable to that from the Periostat® tablets, and well below the potential antibiotic effect concentration (1000 ng/ml). The mean $C_{min}$ (177 ng/ml at 24-hour time point) is well above the minimum effective plasma concentration (100 ng/ml). Individual pharmacokinetic data from both 75/25 IR/DR 40 mg capsules and Periostat® 20 mg tablets show that 75/25 IR/DR 40 mg capsules provide more consistent in vivo performance in terms of less frequency of high peak plasma concentration (>1000 ng/ml) and low plasma concentration (<100 ng/ml) at the end of each dosing.

Figure 5:
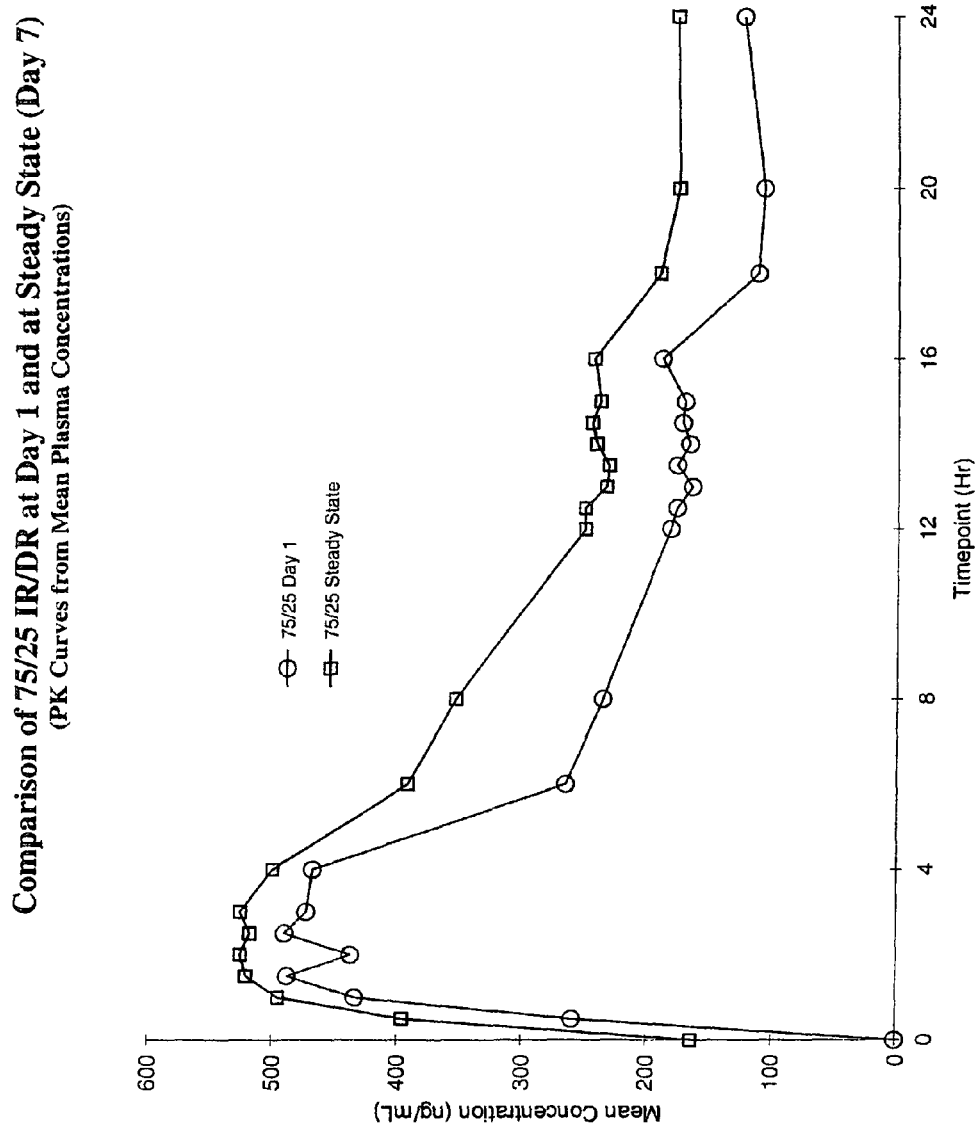
FIG. 5 represents the pharmacokinetic profiles of 75:25 IR:DR (40 mg.) formulation at day 1 and day 7 (steady state) in humans.

FIGS. 5 and 6 show two aspects of results obtained from the study. FIG. 5 compares the PK profiles of 75:25 IR:DR 40 mg doxycycline formulations over a 24 hour period on Day 1 and also on Day 7 (steady state). FIG. 6 compares the PK profiles of the 75:25 40 mg once daily dosage form and the Periostat® 20 mg (twice daily) dosage forms.

What is claimed is:

1. An oral pharmaceutical composition of doxycycline, which at a once-daily dosage will give steady state blood levels of doxycycline of a minimum of 0.1 µg/ml and a maximum of 1.0 µg/ml, the composition consisting of (i) an immediate release (IR) portion comprising 30 mg doxycycline; (ii) a delayed release (DR) portion comprising 10 mg doxycycline; and optionally, (iii) one or more pharmaceutically acceptable excipients.

2. The composition of claim 1, which at a once-daily dosage will give steady state blood levels of the doxycycline of between 0.3 µg/ml to 0.8 µg/ml.

3. The composition of claim 1, wherein the ratio of IR to DR is from 99:1 to 70:30.

4. The composition of claim 3, wherein the ratio of IR to DR is from 80:20 to 70:30.

5. The composition of claim 4, wherein the ratio of IR to DR is 75:25.

6. The composition of claim 1, which is in the form of a granule, tablet, pellet, powder, sachet, capsule, gel, dispersion or suspension.

7. The composition of claim 1, which is in a dosage form of a combination of pellets.

8. The composition according to claim 1, wherein the DR portion comprises at least one enteric polymer.

9. The composition of claim 8, wherein the enteric polymer is cellulose acetate phthalate; hydroxypropyl methylcellulose phthalate; polyvinyl acetate phthalate; hydroxypropyl methylcellulose acetate succinate; cellulose acetate trimellitate; hydroxypropyl methylcellulose succinate; cellulose acetate succinate; cellulose acetate hexahydrophthalate;

cellulose propionate phthalate; a copolymer of methylmethacrylic acid and methyl methacrylate; a copolymer of methyl acrylate, methylmethacrylate and methacrylic acid; a copolymer of methylvinyl ether and maleic anhydride; ethyl methyacrylate -methylmethacrylate-chlorotrimethylammonium ethyl acrylate copolymer; zein; shellac; poly(methacylic acid-co-ethyl acrylate) 1:1, or combinations thereof.

10. The composition according to claim 1, wherein the DR formulation is in the form of granules, pellets, or tablet.

11. The composition according to claim 1, wherein the one or more pharmaceutically acceptable excipients is incorporated in the IR portion, the DR portion, or both.

12. The composition of claim 11, wherein the one or more pharmaceutically acceptable excipients is a binder, a disintegration agent, a filling agent, a surfactant, a solubilizer, a stabilizer, and combinations thereof.

13. The composition of claim 12, wherein the binder is selected from the group consisting of methylcellulose, hydroxyethyl cellulose, hydroxypropyl cellulose, hydroxypropyl methylcellulose, polyvinylpyrrolidone, and polyvinylpyrrolidone/vinyl acetate copolymer.

14. The composition of claim 12, wherein the disintegration agent is selected from the group consisting of cornstarch, pregelatinized starch, cross-linked carboxymethylcellulose, sodium starch glycolate, and cross-linked polyvinylpyrrolidone.

15. The composition of claim 12, wherein the filling agents are selected from the group consisting of lactose, calcium carbonate, calcium phosphate, calcium sulfate, microcrystalline cellulose, dextran, starches, sucrose, xylitol, lactitol, mannitol, sorbitol, sodium chloride, and polyethylene glycol.

16. The composition of claim 12, wherein the surfactants are selected from the group consisting of sodium lauryl sulfate, sorbitan monooleate, polyoxyethylene sorbitan monooleate, bile salts, and glyceryl monostearate.

17. The composition of claim 12, wherein the solubilizers are selected from the group consisting of citric acid, succinic acid, fumaric acid, malic acid, tartaric acid, maleic acid, glutaric acid, sodium bicarbonate, and sodium carbonate.

18. The composition of claim 12, wherein the stabilizers are selected from the group consisting of antioxidation agents, buffers, and acids.

19. A method for treating rosacea in a mammal in need thereof, comprising administering an oral pharmaceutical composition of doxycycline comprising, which at a once-daily dosage will give steady state blood levels of doxycycline of a minimum of 0.1 µg/ml and a maximum of 1.0 µg/ml, the composition consisting of (i) an immediate release (IR) portion comprising 30 mg doxycycline; (ii) a delayed release (DR) portion comprising 10 mg doxycycline; and optionally, (iii) one or more pharmaceutically acceptable excipients.

20. The method of claim 19, wherein the mammal is a human.

21. The method of claim 19, which at a once-daily dosage, administration of the composition will give steady state blood levels of the doxycycline of between 0.3 µg/ml to 0.8 µg/ml.

22. A process for preparing a once-daily oral pharmaceutical composition according to claim 1, which will give steady state blood levels of the tetracycline of a minimum of 0.1 µg/ml and a maximum of 1.0 µg/ml, comprising combining (i) an immediate release (IR) portion comprising 30 mg doxycycline; (ii) a delayed release (DR) portion comprising 10 mg doxycycline; and optionally, (iii) one or more pharmaceutically acceptable excipients.

23. A delayed-release tablet of doxycycline, which at a once-daily dosage will give steady state blood levels of doxycycline of a minimum of 0.1 µg/ml and a maximum of 1.0 µg/ml, the tablet consisting of (i) an immediate release (IR) portion comprising 30 mg doxycycline in the form of tablet; (ii) a delayed release (DR) portion comprising 10 mg doxycycline; and, optionally, (iii) one or more pharmaceutically acceptable excipients.

24. The delayed-release tablet of claim 23, wherein the delayed release (DR) portion is present as a core and the immediate-release (IR) portion as an outer layer atop the core.

25. The delayed-release tablet of claim 23, which at a once-daily dosage will give steady state blood levels of the doxycycline of between 0.3 µg/ml to 0.8 µg/ml.

26. The delayed-release tablet of claim 23, wherein the one or more pharmaceutically acceptable excipients is incorporated in the IR portion, the DR portion, or both.

27. The delayed-release tablet of claim 23, wherein the one or more pharmaceutically acceptable excipients is a binder, a disintegration agent, a filling agent, a surfactant, a solubilizer, a stabilizer, and combinations thereof.

28. A method for treating rosacea in a mammal in need thereof, comprising administering to the mammal a delayed-release tablet of doxycycline, which at a once-daily dosage will give steady state blood levels of doxycycline of a minimum of 0.1 µg/ml and a maximum of 1.0 µg/ml, wherein the tablet consisting of (i) an immediate release (IR) portion comprising 30 mg doxycycline in the form of tablet; (ii) a delayed release (DR) portion comprising 10 mg doxycycline; and optionally, (iii) one or more pharmaceutically acceptable excipients.

29. The method of claim 28, wherein the mammal is a human.

* * * * *

(12) INTER PARTES REVIEW CERTIFICATE (80th)
United States Patent (10) Number: US 8,206,740 K1
Chang et al. (45) Certificate Issued: May 13, 2015

(54) ONCE DAILY FORMULATIONS OF TETRACYCLINES

(75) Inventors: Rong-Kun Chang; Arash Raoufinia; Niraj Shah

(73) Assignee: TCD ROYALTY SUB, LLC

Trial Number:

IPR2013-00368 filed Jun. 20, 2013

Petitioner: Amneal Pharmaceuticals, LLC

Patent Owner: TCD Royalty Sub, LLC

Inter Partes Review Certificate for:

Patent No.: 8,206,740
Issued: Jun. 26, 2012
Appl. No.: 12/155,676
Filed: Jun. 6, 2008

The results of IPR2013-00368 are reflected in this inter partes review certificate under 35 U.S.C. 318(b).

INTER PARTES REVIEW CERTIFICATE
U.S. Patent 8,206,740 K1
Trial No. IPR2013-00368
Certificate Issued May 13, 2015

AS A RESULT OF THE INTER PARTES REVIEW PROCEEDING, IT HAS BEEN DETERMINED THAT:

Claims 1, 2, 5-15 and 19-22 are found patentable.

\* \* \* \* \*